US009506036B2

(12) United States Patent
Fryer

(10) Patent No.: US 9,506,036 B2
(45) Date of Patent: Nov. 29, 2016

(54) DIFFERENTIATION OF HUMAN EMBRYONIC STEM CELLS

(75) Inventor: Benjamin Fryer, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 383 days.

(21) Appl. No.: 13/211,951

(22) Filed: Aug. 17, 2011

(65) Prior Publication Data

US 2012/0052571 A1 Mar. 1, 2012

Related U.S. Application Data

(60) Provisional application No. 61/378,448, filed on Aug. 31, 2010.

(51) Int. Cl.
*C12N 5/071* (2010.01)

(52) U.S. Cl.
CPC ......... *C12N 5/0678* (2013.01); *C12N 2500/34* (2013.01); *C12N 2501/115* (2013.01); *C12N 2501/19* (2013.01); *C12N 2501/727* (2013.01); *C12N 2506/02* (2013.01); *C12N 2533/54* (2013.01)

(58) Field of Classification Search
CPC ............ C12N 5/0678; C12N 2500/34; C12N 2501/15; C12N 2501/16; C12N 2501/19; C12N 2506/02
USPC .................................................. 435/366, 377
See application file for complete search history.

(56) References Cited

U.S. PATENT DOCUMENTS

| 3,209,652 | A | 10/1965 | Burgsmueller |
| 3,845,641 | A | 11/1974 | Waller |
| 3,935,067 | A | 1/1976 | Thayer |
| 4,499,802 | A | 2/1985 | Simpson |
| 4,537,773 | A | 8/1985 | Shenvi |
| 4,557,264 | A | 12/1985 | Hinsch |
| 4,737,578 | A | 4/1988 | Evans et al. |
| 5,215,893 | A | 6/1993 | Mason et al. |
| 5,449,383 | A | 9/1995 | Chatelier et al. |
| 5,525,488 | A | 6/1996 | Mason et al. |
| 5,567,612 | A | 10/1996 | Vacanti et al. |
| 5,665,568 | A | 9/1997 | Mason et al. |
| 5,686,090 | A | 11/1997 | Schilder et al. |
| 5,713,957 | A | 2/1998 | Steele et al. |
| 5,716,810 | A | 2/1998 | Mason et al. |
| 5,718,922 | A | 2/1998 | Herrero-Vanrell |
| 5,759,830 | A | 6/1998 | Vacanti et al. |
| 5,770,417 | A | 6/1998 | Vacanti et al. |
| 5,780,454 | A | 7/1998 | Adams et al. |
| 5,834,308 | A | 11/1998 | Peck et al. |
| 5,843,780 | A | 12/1998 | Thomson |
| 5,888,816 | A | 3/1999 | Coon et al. |
| 5,908,782 | A | 6/1999 | Marshank et al. |
| 5,914,262 | A | 6/1999 | MacMichael et al. |
| 5,942,435 | A | 8/1999 | Wheeler |
| 6,001,647 | A | 12/1999 | Peck et al. |
| 6,022,743 | A | 2/2000 | Naughton et al. |
| 6,083,903 | A | 7/2000 | Adams et al. |
| 6,087,113 | A | 7/2000 | Caplan et al. |
| 6,200,806 | B1 | 3/2001 | Thomson |
| 6,261,549 | B1 | 7/2001 | Fernandez et al. |
| 6,281,012 | B1 | 8/2001 | McIntosh et al. |
| 6,297,217 | B1 | 10/2001 | Adams et al. |
| 6,306,424 | B1 | 10/2001 | Vyakarnan et al. |
| 6,328,960 | B1 | 12/2001 | McIntosh et al. |
| 6,331,298 | B1 | 12/2001 | Ferguson et al. |
| 6,333,029 | B1 | 12/2001 | Vyakarnam et al. |
| 6,365,149 | B2 | 4/2002 | Vyakarnam et al. |
| 6,413,773 | B1 | 7/2002 | Ptasznik et al. |
| 6,436,704 | B1 | 8/2002 | Roberts et al. |
| 6,458,589 | B1 | 10/2002 | Rambhatla |
| 6,458,593 | B1 | 10/2002 | Musick et al. |
| 6,509,369 | B2 | 1/2003 | Scott et al. |
| 6,521,427 | B1 | 2/2003 | Evans |
| 6,534,084 | B1 | 3/2003 | Vyakarnam et al. |
| 6,599,323 | B2 | 7/2003 | Melican et al. |
| 6,617,152 | B2 | 9/2003 | Bryhan et al. |
| 6,617,317 | B1 | 9/2003 | Adams et al. |
| 6,626,950 | B2 | 9/2003 | Brown et al. |
| 6,642,048 | B2 | 11/2003 | Xu |
| 6,656,488 | B2 | 12/2003 | Yi et al. |
| 6,670,127 | B2 | 12/2003 | Evans |
| 6,703,017 | B1 | 3/2004 | Peck et al. |
| 6,713,446 | B2 | 3/2004 | Gupta |
| 6,793,945 | B2 | 9/2004 | Bathurst et al. |
| 6,800,480 | B1 | 10/2004 | Bodnar et al. |

(Continued)

FOREIGN PATENT DOCUMENTS

| CN | 1389565 A | 7/2002 |
| CN | 1602351 A | 3/2005 |

(Continued)

OTHER PUBLICATIONS

Ratanasavanh et al, J. Histochem. Cytochem. 34:527-533, 1986.*
Gualdi et al, Genes & Development 10:1670-1682, 1996.*
NIH Stem Cells: Scientific Progress and Future Research Directions, Department of Health and Human Services, Chapter I, pp. 1-4, Jun. 2001.*
Jaenisch et al, Cell, 132: 567-582, 2008.*
D'Amour et al, Nature Biotechnol. 23(12):1534-1541, 2005.*
D'Amour et al, Nature Biotechnol. 24(11):1391-1401, 2006.*
McLean et al, Stem Cells 25(1):29-38, 2007.*
Roelandt et al, PLoS ONE 5(8):e12101, pp. 1-11, available online Aug. 11, 2010.*
Zulewski et al, Diabetes 50:521-533, 2001.*
Ungrin et al, PLoS ONE 3(2):e1565, pp. 1-12, 2008.*

(Continued)

*Primary Examiner* — Kevin Hill
(74) *Attorney, Agent, or Firm* — Lois A. Gianneschi

(57) ABSTRACT

The present invention provides methods to promote the differentiation of pluripotent stem cells into insulin producing cells. In particular, the present invention provides a method to produce a population of cells, wherein greater than 80% of the cells in the population express markers characteristic of the definitive endoderm lineage.

6 Claims, 9 Drawing Sheets

(56) References Cited

U.S. PATENT DOCUMENTS

| | | |
|---|---|---|
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico et al. |
| 2007/0264713 A1 | 11/2007 | Terstegge et al. |
| 2008/0091234 A1 | 4/2008 | Kladakis et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0053182 A1 | 2/2009 | Ichim et al. |
| 2009/0092586 A1* | 4/2009 | Verfaillie et al. ............ 424/93.7 |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0151560 A1 | 6/2011 | Xu |
| 2011/0229441 A1 | 9/2011 | Benchoua et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | 9219759 A2 | 2/1992 |
| WO | 9847892 A1 | 10/1998 |
| WO | 9920741 A1 | 4/1999 |
| WO | 0029549 A1 | 5/2000 |
| WO | 0123528 A1 | 4/2001 |
| WO | 0151616 A2 | 7/2001 |
| WO | 0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | 0305049 A1 | 6/2003 |
| WO | 03054169 A1 | 7/2003 |
| WO | 03062405 A2 | 7/2003 |
| WO | 03095452 A1 | 11/2003 |
| WO | 03102134 A2 | 12/2003 |
| WO | 03103972 A1 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |

(56) References Cited

FOREIGN PATENT DOCUMENTS

| | | |
|---|---|---|
| WO | 2004087885 A2 | 10/2004 |
| WO | 2004090110 A2 | 10/2004 |
| WO | 2004067001 A1 | 12/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007101130 A2 | 9/2007 |
| WO | 2007103282 A1 | 9/2007 |
| WO | 2007127927 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096049 A1 | 8/2009 |
| WO | 2009096902 A1 | 8/2009 |
| WO | 2009101407 A2 | 8/2009 |
| WO | 2009105570 A2 | 8/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |

OTHER PUBLICATIONS

Agarwal et al, Stem Cells 26:1117-1127, 2008.*
Klimanskaya et al, Lancet 365:1636-1641, 2005.*
Koblas et al, Transplantation Proc. 40:415-418, 2008.*
Toso et al, Am. J. Transplantation 8:701-706, 2008.*
Schaefer-Graf et al, Am. J. Obstet. Gynecol. 182:313-320, 2000.*
Abe, et al., Evidence That PI3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of PI3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

(56) References Cited

OTHER PUBLICATIONS

Barclay, et al., The Leucocyte Antigen Facts Book, The Leucocyte Antigen Facts Book, 1997, Textbook, 2[sup] edition, Academic Press.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.
Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymal Stem Cells in Pancreatic Islet Beta-Cells, World Journal of Gastroenterology, Oct. 15, 2004, pp. 3016-3020.
Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone—expressing endocrine cells from human embryonic stem cells, Nature Biotechnology, Oct. 19, 2006, 1392-1401, 24-11, Nature Publishing Group, US.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.

(56) References Cited

OTHER PUBLICATIONS

Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331 XP002699177, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al, Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35 XP025995041, vol. 326, No. 1.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

(56) References Cited

OTHER PUBLICATIONS

Herrera, Adult-Insulin-and Glucagon-Producing Cells Differentiate from Two Independent Cell Lineages, Development, 2000, pp. 2317-2322 XP001004766, vol. 127, No. 11.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 56.
Hussain, et al., Stem-Cell Therapy for Diabetes Mellitus, Lancet, 2004, pp. 203-205, vol. 364.
Ianus et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Biointerphases, Dec. 2009, pp. 6979.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova, et al, EphA-Ephrin-A-Mediated Beta Cell Communication Regulates Insulin Secretion from Pancreatic Islets, Cell, Apr. 20, 2007, pp. 359-370, vol. 129.
Koyangi et al., Inhibition of the Rho/ROCK Pathway Reduces Apoptosis During Transplantation of Embryonic Stem Cell-Derived Neural Precursors, Journal of Neuroscience Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Ku et al., Committing Embryonic Stem Cells to Early Endocrine Pancreas in Vitro, Stem Cells, 2004, 1205-1217, 22, AlphaMed Press.
Kubo et al., Development of definitive endoderm from embryonic stem cells in culture, Development, 2004, 1651-1662, 131, The Company of Biologists.
Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

(56) References Cited

OTHER PUBLICATIONS

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., Protein Kinase A- and C- Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Pluripotency Can be Rapidly and Efficiently Induced in Human Amniotic Fluid-Derived Cells, Human Molecular Genetics, 2009, pp. 4340-4349, vol. 18, No. 22.
Lilja et al., Cyclin-dependent Kinase 5 Promotes Insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Loh, et al., Genomic Approaches to Deconstruct Puripotency, Annu Rev Genomics Hum Genet, 2011, pp. 165-185, vol. 12.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, 1389-1394, 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.
Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyronic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.

(56) References Cited

OTHER PUBLICATIONS

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nicholas et al., A Method for Single-Cell Sorting and Expansion of Genetically modified Human Embryonic Stem Cells, Stem Cells and Development, 2007, 109-117, 16, Mary Ann Liebert, Inc.

Nishimura, et al., Expression of MafA in Pancreatic Progenitors is Detrimental for Pancreatic Development, Developmental Biology, 2009, pp. 108-120, vol. 333.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Ouziel-Yahalom, et al., Expansion and Redifferentiation of Adult Human Pancreatic islet Cells, Biochemical and Biophysical Research Communications, 2006, pp. 291-298, vol. 341.

Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.

Pancreatic Endoderm, http://www.rndsystems.com/molecule_group.aspx?g=801&r, 1 page web printout (dated May 31, 2013).

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al., Coming CellBIND Surface: An Improved Surface for Enhanced Cell Attachment, Corning Technical Report, 2005, 8 page report, XP002530385.

Paris, et al., Equine Embryos and Embryonic Stem Cells: Defining Reliable Markers of Pluripotency, Theriogeneology, 2010, pp. 516-524, vol. 74.

Peerani, et al., Niche-Mediated Control of Human Embryonic Stem Cell Self-Renewal and Differentiation, The EMBO Journal, 2007, pp. 4744-4755, vol. 26.

Phillips, et al., Attachment and Growth of Human Embryonic Stem Cells on Microcarriers, Journal of Biotechnology, 2008, pp. 24-32, vol. 138.

Phillips, et al., Directed Differentiation of Human Embryonic Stem Cells into the Pancreatic Endocrine Lineage, Stem Cells and Development, 2007, pp. 561-578 XP009090586, vol. 16, No. 4.

Pouton, et al., Embryonic Stem Cells as a Source of Models for Drug Discovery, Nature Reviews Drug Discovery, Aug. 2007, pp. 1474-1776, vol. 6, No. 8.

Prichard, et al., Adult Adipose Derived Stem Cell Attachment to Biomaterials, Biomaterials, 2006, pp. 936-946, vol. 28, No. 6.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Ptasznik, et al., Phosphatidylinositol 3-Kinase Is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, http://www.rndsystems.com/molecule_group.aspx?r=1&g-3041, 2 page web printout (dated May 31, 2013).

Rajagopal, et al., Insulin Staining of ES Cell Progeny from Insulin Uptake, Science, Jan. 17, 2003, pp. 363, vol. 299.

RAO, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rebollar, et al., Proliferation of Aligned Mammalian Cells on Laser-Nanostructured Polystyrene, Biomaterials, 2008, pp. 1796-1806, vol. 29.

Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, 399-404, 18, Nature America Inc.

Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.

Rezania, Production of Functional Glucagon-Secreting-Cells from Human Embryonic Stem Cells, Diabetes, 2011, pp. 239-247, vol. 60, Issue 1.

Richards et al., Comparative Evaluation of Various Human Feeders for Prolonged Undifferentiated Growth of Human Embryonic Stem Cells, Stem Cells, 2003, 546-556, 21, AlphaMed Publlishing.

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

Ricordi et al., Automated Method for Isolation of Human Pancreatic Islets, Diabetes, Apr. 1988, 413-420, 37, American Diabetes Association.

Ryan, et al., Clinical Outcomes and Insulin Secretion After Islet Transplantation with the Edmonton Protocol, Diabetes, Apr. 2001, pp. 710-719, vol. 50.

Sakaguchi, et al., Integration of Adult mesenchymal Stem Cells in the CNS, Society for Neuroscience Abstract Viewer and Itineray Planner, 2002, XP002519394, Program 237.18.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savino et al., Generation of Interleukin-6 Receptor Antagonists by Molecular-Modeling Guided Mutagenesis of Residues Important for gp130 Activation, EMBO Journal, 1994, 1357-1367, 13-6, IT.

(56) References Cited

OTHER PUBLICATIONS

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Schuldiner, et al., Induced Neuronal Differentiation of Human Embryonic Stem Cells, Brain Research, 2001, pp. 201-205, vol. 913.

Scullica, et al., Diagnosis and Classification of Macular Degenerations: an Approach Based on Retinal Function Testing, Documenta Ophthalmologica, 2001, pp. 237-250, vol. 102.

Seaberg et al., Clonal identification of multipotent precursors from adult~mouse pancreas that generate neural and pancreatic lineages, Nature Biotechnology, Sep. 2004, 1115-1124, 22, Nature Publishing Group.

Segev, et al., Differentiation of Human Embryonic Stem Cells into Insulin-Producing Clusters, Stem Cells, Jan. 1, 2004, pp. 265-274.

Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.

Shackleton, et al., Generation of a Functional Mammary Gland from a Single Stem Cell, Nature, Jan. 5, 2006, pp. 84-88, XP002567665, vol. 439.

Shamblott et al., Derivation of pluripotent stem cells from cultured human primordial germ cells, Developmental Biology, Nov. 1998, 13726-13731, 95, National Academy of Sciences.

Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.

Shim, et al., Directed Differentiation of Human Embryonic Stem Cells Towards a Pancreatic Cell Fate, Diabetologia, 2007, pp. 1228-1238, vol. 50.

Schindler et al., A synthetic nanofibrillar matrix promotes in vivo-like organization and morphogenesis for cells in culture, Biomaterials, Apr. 18, 2005, 5624-5631, 26, Elsevier.

Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by FACS Sorting and Their Characterization, Stem Cells and Development, 2006, 61-69, 15, Mary Ann Liebert, Inc.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.

Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.

Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.

Spence, et al., Translation Embryology: Using Embryonic Principles to Generate Pancreatic Endocrine Cells from Embryonic Stem Cells, Developmental Dynamics, 2007, pp. 3218-3227, vol. 236.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Acid Signaling is Required for a Critical Early Step in Zebrafish Pancreatic Development, Current Biology, 2002, pp. 1215-1220, vol. 12, Issue 14.

Stojkovic et al., An Autogeneic Feeder Cell System That Efficiently Supports Growth of Undifferentiated Human Embryonic Stem Cells, Stem Cells, 2005, 306-314, 23, AlphaMed Press.

Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.

Sugiyama, et al., Fluorescence-Activated Cell Sorting Purification of Pancreatic Progenitor Cells, Diabetes, Obesity and Metabolism, 2008, pp. 179-185, vol. 10, Supplement 4.

Suh, et al., Characterization of His-X3-His Sites in a-Helices of Synthetic Metal-Binding Bovine Somatotropin, Protein Engineering, 1991, pp. 301-305, vol. 4, No. 3.

Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.

Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.

Takahashi, et al., Homogenous Seeding of Mesenchymal Stem Cells into Nonwoven Fabric for Tissue Engineering, Tissue Engineering, 2003, pp. 931-938, vol. 9, No. 5.

Takahashi, et al., Induction of Pluripotent Stem Cells from Adult Human Fibroblasts by Defined Factors, Cell, 2007, pp. 861-872, vol. 131.

Takehara, et al., Rho-Associated Kinase Inhibitor Y-27632 Promotes Survival of Cynomolgus Monkey Embryonic Stem Cells, Molecular Human Reproduction, 2008, pp. 627-634, vol. 14, No. 11.

Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.

Teare, et al., Cellular Attachment to Ultraviolet Ozone Modified Polystyrene Surfaces, Langmuir, 2000, pp. 2818-2824, vol. 16.

Thomson et al., Embryonic Stem Cell Lines Derived from Human Blastocysts, Science, Nov. 6, 1998, 1145-1147, 282, HighWire Press.

Thomson et al., Isolation of a primate embryonic stem cell line, Developmental Biology, Aug. 1995, 7844-7848, 92, Proc. Natl. Acad. Sci, US.

Thomson et al., Primate Embryonic Stem Cells, Current Topics in Developmental Biology, 1998, 133-154, 38, Academic Press, US.

(56) References Cited

OTHER PUBLICATIONS

Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al, Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vodicka, et al, The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniF7rot [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

(56) References Cited

OTHER PUBLICATIONS

Zhang, Jie, The Differentiation of Bone Marrow Mesenchymal Stem Cells into Retina in Rat Eye and the Therapeutical Effect on Severe Injured Retina, a Doctoral Thesis of Chinese PLA Acadamey of Military Medical Sciences, 2003, 1-127, 1-127 (with English Abstract).

Zhang et al, Highly Efficient Differentiation of Human ES Cells and iPS Cells into Mature Pancreatic Insulin-Producing Cells, Cell Research, 2009, pp. 429-438, vol. 19, Issue 14.

Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.

Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zorn, et al., Vertebrate Endoderm Development and Organ Formation, Annual Review Cell Development Biology, 2009, pp. 221-251, vol. 25.

Zubaty, et al., Transplantation of Mesenchymal Stem Cells into RCS Rats for Retinal Repair, Investigative Ophthalmology and Visual Science, 2005, pp. 4160-B518, vol. 46, Supplement S.

Ali, et al., Exploitation of Protein Kinase C: A Useful Target for Cancer Therapy, Cancer Treatment Reviews, 2009, pp. 1-8, vol. 35.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Best, et al., Embryonic Stem Cells to Beta-Cells by Understanding Pancreas Development, Molecular and Cellular Endorinology, 2008, pp. 86-94, vol. 288.

Bo, et al., Research Progress of Pancreatic Islet Development and Pancreatic Stem Cells, Journal of Clinical Surgery, 2009, pp. 208-210, vol. 17, No. 3.

Brevini et al, Embryonic Stem Cells in Domestic Animals, Embryonic Stem Cells in Domestic Animals, 2010, 544-550, 74.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Chetty, et al., A Simple Tool to Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.

D'Amour et al, Production of pancreatic hormone, Production of pancreatic hormone, Nature Biotechnology, 2006, 1392-1401, 24.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.

Foster, et al., Differentiation of Transplanted Microencapsulated Fetal Pancreatic Cells, Experimental Transplantation, Jun. 15, 2007, pp. 1440-1448, vol. 83, No. 11.

Gibco, Solutions for Life Science Research and Drug Discovery, Catalogue Cell Culture Products, 2004-2005, pp. 1-4E, 281406 26 5 27.

Gordon Weir, Do stem cells hold the key to creation of a cure for diabetes?, Diabetes Voice, 2008, pp. 29-31, Edition 53, No. 2.

Gregg Duester, Retionoic Acid Synthesis and Signaling During Early Organogenesis, Cell, 2008, pp. 921-931, vol. 134.

Hainsworth, et al., Retinal Capillar Basement Membrane Thickening in a Porcine Model of Diabetes Mellitus, Comp Med, 2002, pp. 523-529, vol. 52.

Hay, et al., Highly Efliicient Differentiation of hESCs to Functional Hepatic Endoderm Requires ActivinA and Wnt3a Signaling, PNAS, 2008, pp. 12301-12306, vol. 105, No. 34.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Karvonen, et al., Incidence of Childhood Type 1 Diabetes Worldwide, Diabetes Care, 2000, pp. 1516-1526, vol. 23, No. 10.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Larsen, et al., Use of the Gootingen Minipig as a Model of Diabetes, with Special Focus on Type 1 Diabetes Research, ILAR Journal, 2004, pp. 303-313, vol. 45, No. 3.

Lee, et al., PKC- Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

Munoz et al, Conventional pluripotency markers are unspecific for bovine embryonic-derived cell-lines, Theriogenology, 2008, 1159-1164, vol. 69.

Paris, et al, Embryonic Stem Cells in Domestic Animals, Equine embryos and embryonic stem cells: Defining reliable markers of pluripotency, Theriogenology, 2010, 516-524, vol. 74.

Perrier, et al., Derivation of Midbrain Dopamine Neurons from Human Embryonic Stem Cells, PNAS, Aug. 24, 2004, pp. 12543-12548, vol. 101, No. 34.

Ramiya, et al., Reversal of Insulin-Dependent Diabetes Using Islets Generated in vitro from Pancreatic Stem Cells, Nature Medicine, 2000, pp. 278-281, vol. 6.

Rezania, e al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Ross, et al., Cytochrome P450s in the Regulation of Cellular Retinoic Acid Metabolism, Annu. Rev. Nutr., 2011, pp. 65-87, vol. 31.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.

Soria, et al., From Stem Cells to Beta Cells: New Strategies in Cell Therapy of Diabetes Mellitus, Diabetologia, 2001, pp. 407-415, vol. 44.

Stafford, et al., Retinoids Signal Directly to Zebrafish Endoderm to Specify Insuilin-Expressing B-cells, Development, 2005, pp. 949-956, vol. 133.

Stoffel, et al., Navigating the Pathway from Embryonic Stem Cells to Beta Cells, Seminars in Cell & Developmental Biology, 2004, pp. 327-336, vol. 15.

Suzuken, Differentiation of Multifunctional Stem Cells Using Human Feeder Cells, Research Papers of the Suzuken Memorial Foundation, 2007, pp. 193-197, vol. 24, JP.

Swindle, et al., Swine in Biomedical Research: Management and Models, ILAR News, 1994, pp. 1-5, vol. 36, No. 1.

Tsuchida, et al., Activin Isoforms Signal Through Type I Receptor Serine/Threonin Kinase ALK7, Molecular and Cellular Endocrinology, 2004, pp. 59-65, vol. 22.

White, et al., Complex Regulation of cyp26a1 Creates a Robust Retinoic Acid Gradient in the Zebrafish Embryo, PLOS Biology, 2007, pp. 2522-2533, vol. 5, Issue 11.

Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.

Cao, et al., High Glucose is Necessary for Complete Maturation of Pdx1-VP16-Expressing Hepatic Cells into Functional Insulin-Producing Cells, Diabetes, 2004, pp. 3168-3176, vol. 53.

(56) References Cited

OTHER PUBLICATIONS

Jiang, et al., In Vitro Derivation of Functional Insulin-Producing Cells from Human Embryonic Stem Cells, Cell Research, 2007, pp. 333-344, vol. 17.

Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Wang, et al., Three-Dimensional Differentiation of Embryonic Stem Cells into islet-Like Insulin-Producing Clusters, Tissue Engineering: Part A, 2009, pp. 1941-1952, vol. 15, No. 8.

Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.

Eguizabal, et al., Embryonic Stem Cells/Induced Pluripotent Stem Complete Meiosis from Human Induced Pluripotent Stem Cells, Stem Cells, 2011, pp. 1186-1195, vol. 29.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

Harmon, et al., GDF11 Modulates NGN3+ Islet Progenitor Cell Number and Promotes B-Cell Differentiation in Pancreas Development, Development, 2004, pp. 6163-6174, vol. 131.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Ludwig et al., Defined Culture Media for Human Embryonic Stem Cells, Embryonic Stem Cells, 2007, pp. 1-16, Springer.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Nie, et al., Scalable Passaging of Adherent Human Pluripotent Stem Cells, PLOS One, 2014, pp. 1-9, vol. 9, Issue 1.

Park, et al., Effects of Activin A on Pancreatic Ductal Cells in Streptozotocin-Inducted Diabetic Rats, Experimental Transplantation, 2007, pp. 925-930, vol. 83.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Richards, et al., Development of Defined Media for the Serum-Free Expansion of Primary Keratinocytes and Human Embryonic Stem Cells, Tissue Engineering, 2008, pp. 221-232, vol. 14, No. 3.

Rowley, et al., Meeting Lot-Size Challenges of Manufacturing Adherent Cells for Therapy, Cell Therapies Manufacturing, 2012, pp. 16-22, vol. 10, No. 3.

Schulz, et al., A Scalable System for Production of Functional Pancreatic Progenitors from Human Embryonic Stem Cells, PLOS One, 2012, pp. 1-17, vol. 7, Issue 5.

Sneddon, et al., Self-Renewal of Embryonic-Stem-Cell-Derived Progenitors by Organ-Matched Mesenchyme, Nature, Nov. 29, 2012, pp. 765-770, vol. 491.

Stacpoole, et al., Efficient Derivation of Neural Precursor Cells, Spinal Motor Neurons and Midbr, Nat Protoc, 2012, pp. 1-26, vol. 6, Issue 8.

Vieira, et al., Modulation of Neuronal Stem Cell Differentiation by Hypoxia and Reactive Oxygen Species, Progress in Neurobiology, 2011, pp. 444-455, vol. 93.

Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

Yang, et al., Evaluation of Humam MSCs Cell Cycle, Viability and Differentiation in Micromass Culture, Biorheology, 2006, p. 489-496, vol. 43 (English Abstract Only).

Zalzman, et al., Differentiation of Human Liver-Derived, Insulin-Producing Cells Toward the B-Cell Phenotype, Diabetes, 2005, pp. 2568-2575, vol. 54.

Zuscik, et al., Regulation of Chondrogenesis and Chondrocyte Differentiation by Stress, J Clin Invest, 2008, pp. 429-438, vol. 118, Issue 2.

\* cited by examiner

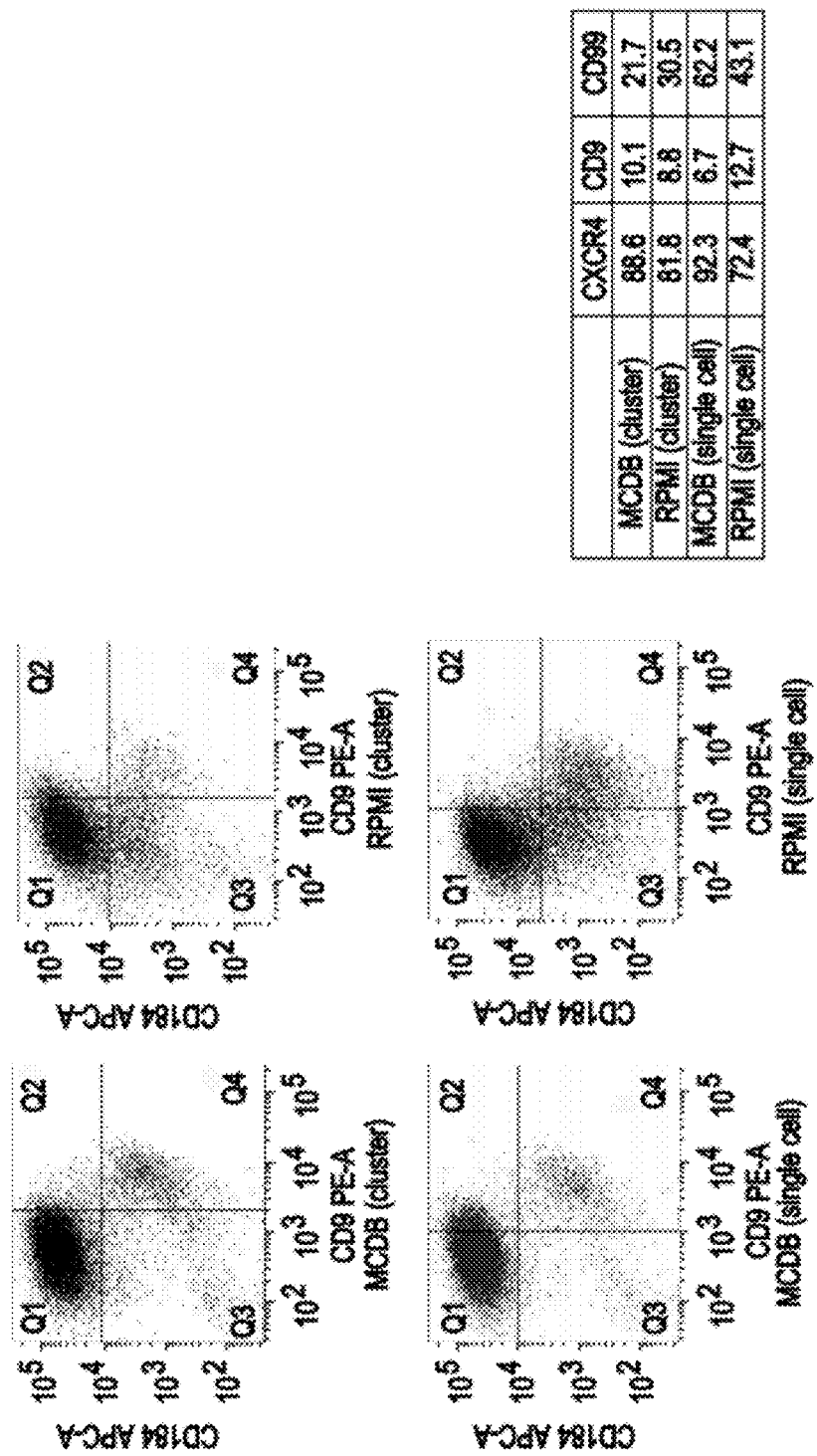

CXCR4

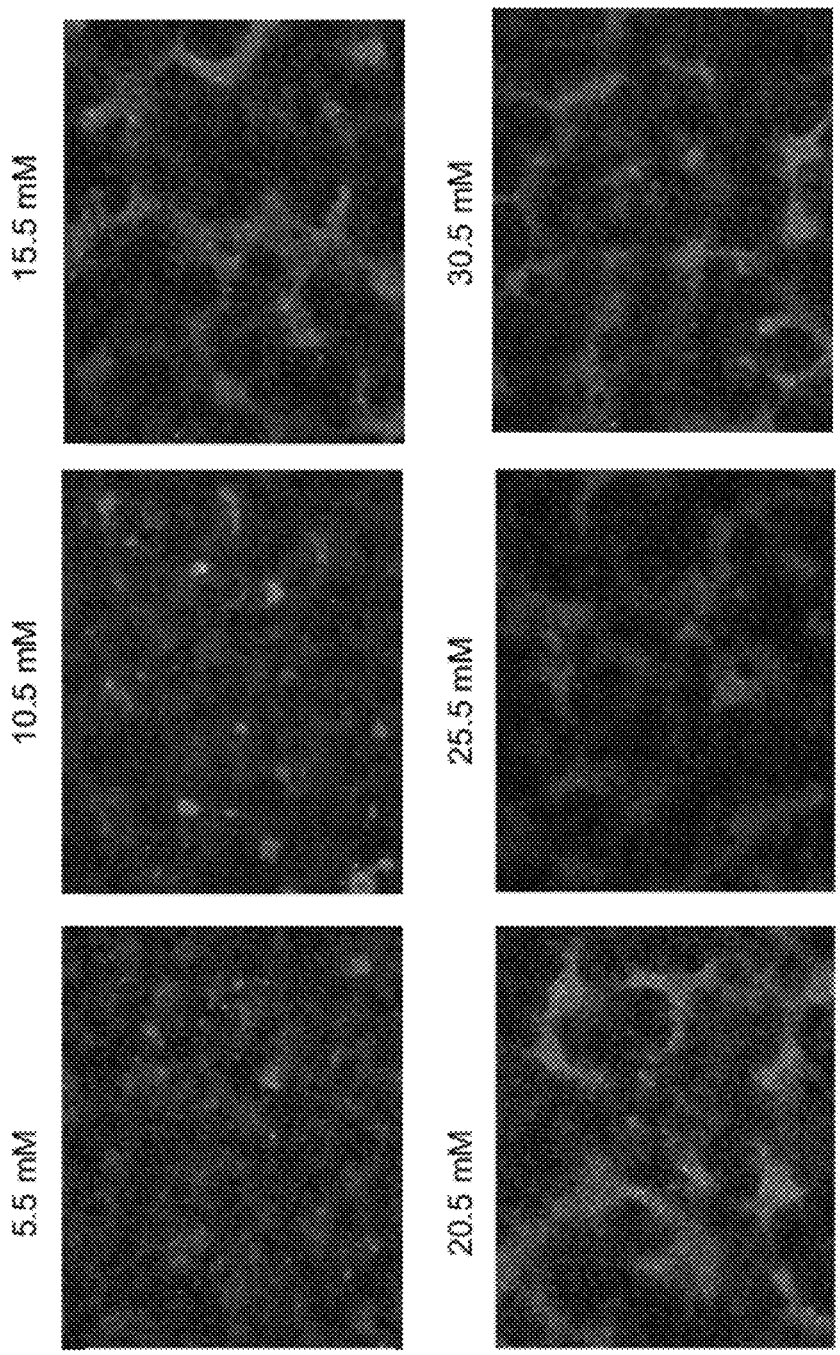

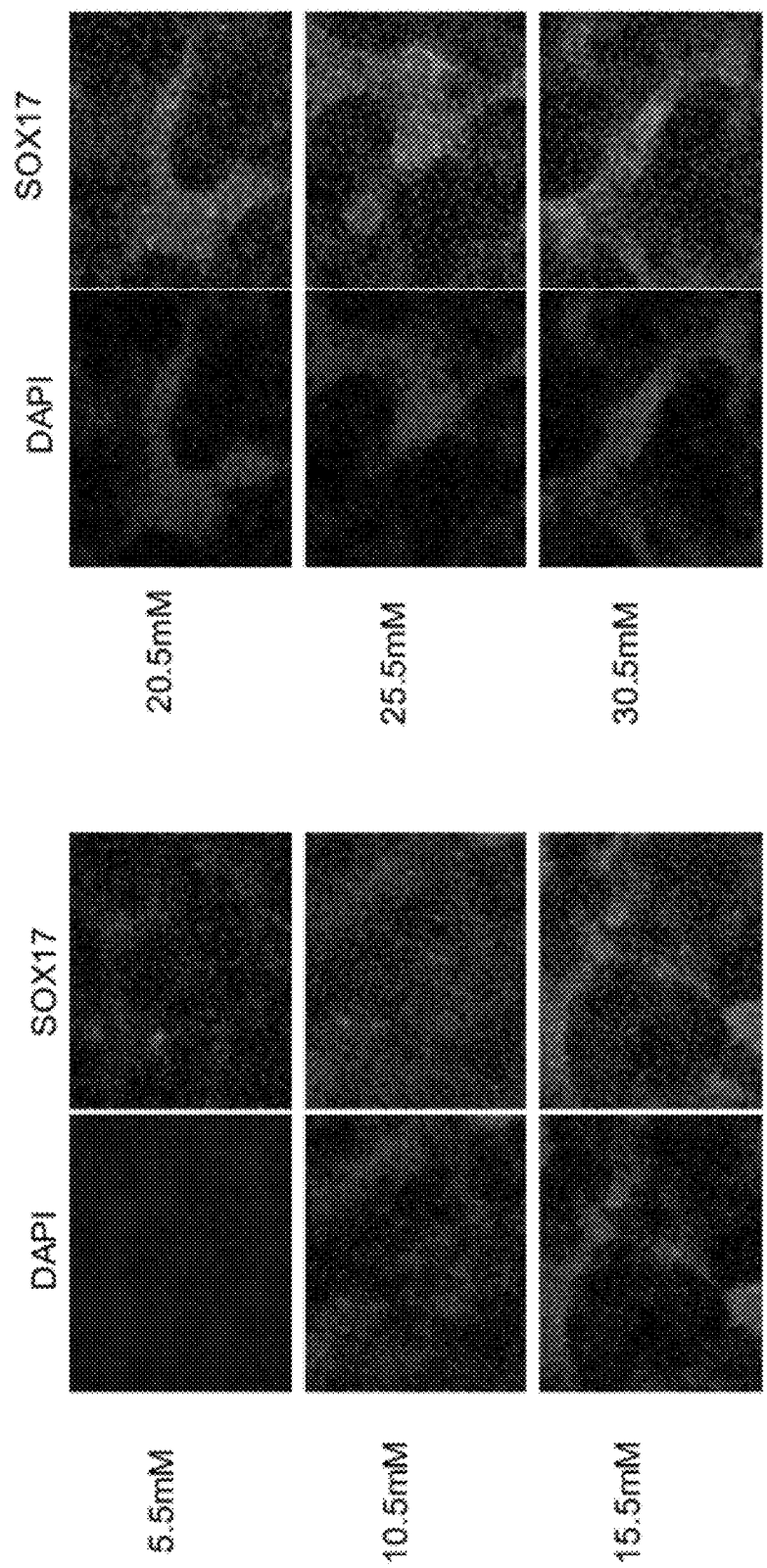

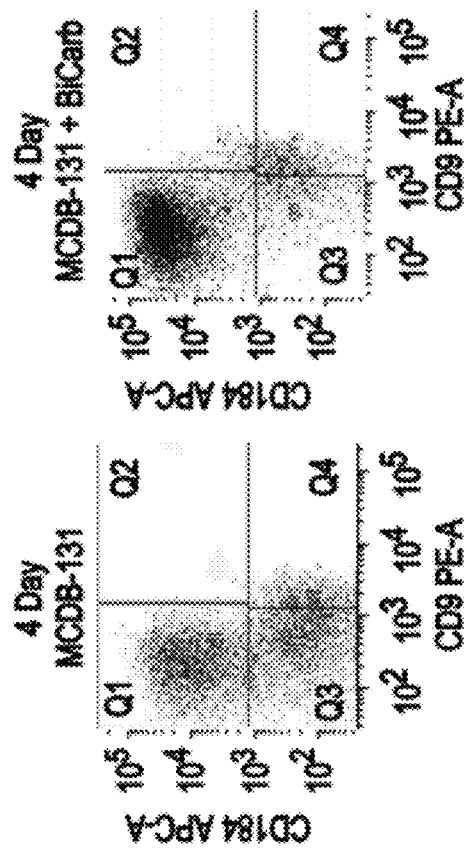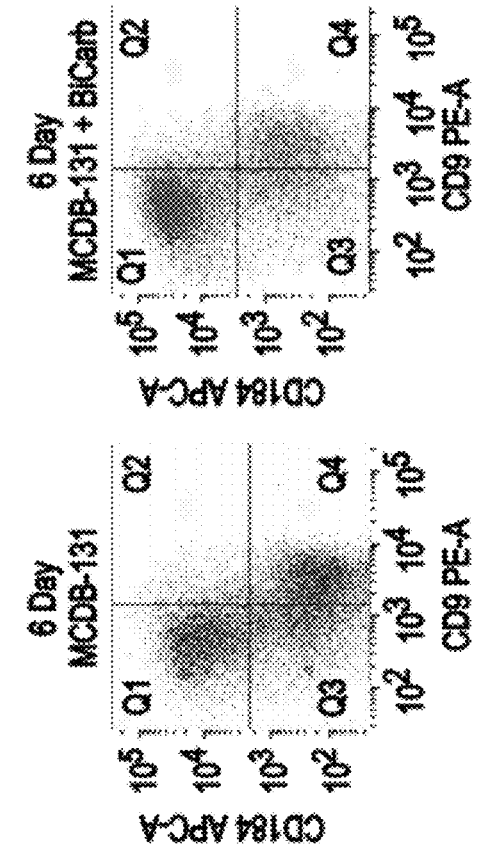
FIG. 7A
FIG. 7B

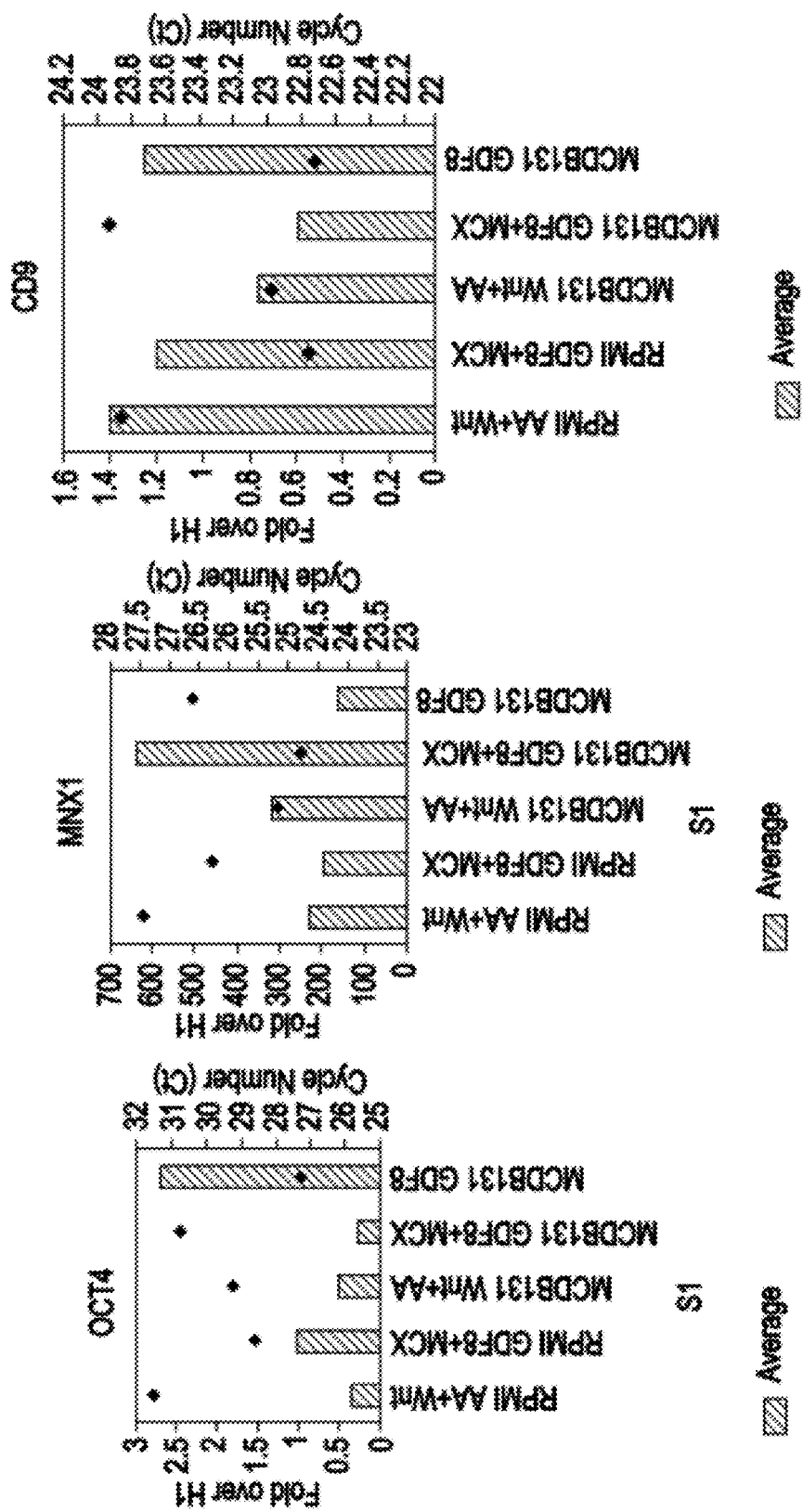

DIFFERENTIATION OF HUMAN EMBRYONIC STEM CELLS

CROSS REFERENCE TO RELATED APPLICATION

The present application claims the benefit of U.S. Provisional Patent Application Ser. No. 61/378,448, filed Aug. 31, 2010, which is incorporated herein by reference in its entirety for all purpose.

FIELD OF THE INVENTION

The present invention provides methods to promote the differentiation of pluripotent stem cells into insulin producing cells. In particular, the present invention provides a method to produce a population of cells, wherein greater than 80% of the cells in the population express markers characteristic of the definitive endoderm lineage.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, p48, Pax6, and Hnf6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into PDX1 positive cells. They observed that TGF-β2 reproducibly yielded a higher proportion of PDX1 positive cells (Genes Cells. 2005 June; 10(6): 503-16.).

Gordon et al. demonstrated the induction of brachyury [positive]/HNF3 beta [positive] endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate PDX1 positive cells. The terminal differentiation was induced by nicotinamide.

There still remains a significant need to develop in vitro methods to generate a functional insulin expressing cell, that more closely resemble a β cell. The present invention takes an alternative approach to improve the efficiency of differentiating human embryonic stem cells toward insulin expressing cells, by generating a population of cells wherein greater than 80% of the cells in the population express markers characteristic of the definitive endoderm lineage.

SUMMARY

In one embodiment, the present invention provides a population of cells, wherein greater than 80% of the cells in the population express markers characteristic of the definitive endoderm lineage.

In one embodiment, the present invention A method for generating a population of cells wherein greater than 80% of the cells in the population express markers characteristic of the definitive endoderm lineage, comprising the steps of:
  a. Culturing a population of pluripotent stem cells,
  b. Differentiating the population of pluripotent stem cells to a population of cells wherein greater than 80% of the cells in the population express markers characteristic of the definitive endoderm lineage in medium wherein the concentration of glucose does not exceed 10.5 mM.

BRIEF DESCRIPTION OF THE DRAWINGS

FIG. 1 shows the FACS analysis of the expression of the proteins indicated in cells of the human embryonic stem cell line H1, differentiated according to the methods disclosed in Example 1.

FIG. 3 shows the effect of medium glucose concentration on CXCR4 expression levels and culture appearance (Panel A), and SOX17 expression in cells of the human embryonic stem cell line H1, differentiated according to the methods disclosed in Example 2.

FIG. 7 shows the effect of medium pH levels on the expression of the genes indicated in cells of the human embryonic stem cell line H1, differentiated according to the second method disclosed in Example 3.

FIG. 8 shows the real-time PCR analysis of the expression of the genes indicated in cells of the human embryonic stem cell line H1, differentiated according to the method disclosed in Example 4.

DETAILED DESCRIPTION

Figure 2B:
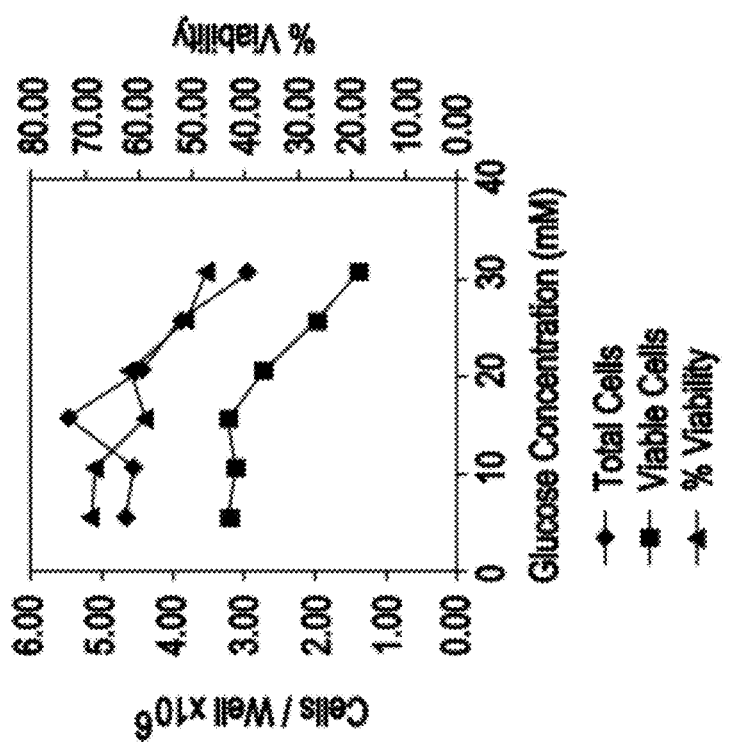
FIG. 2 shows the effect of medium glucose concentration on CXCR4 expression levels (panel B) and cell number and viability (panel B) in cells of the human embryonic stem cell line H1, differentiated according to the methods disclosed in Example 2.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Cells expressing markers characteristic of the definitive endoderm lineage", or "Stage 1 cells", or "Stage 1", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage include pancreatic endoderm cells, primitive gut tube cells, and posterior foregut cells.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine cell", or "Pancreatic hormone expressing cell", or "Cells expressing markers characteristic of the pancreatic endocrine lineage" as used herein, refers to a cell capable of expressing at least one of the following hormones: insulin, glucagon, somatostatin, and pancreatic polypeptide.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra 1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

In one embodiment, pluripotent stem cells may be cultured on a mouse embryonic fibroblast feeder cell layer according to the methods disclosed in Reubinoff et al (Nature Biotechnology 18: 399-404 (2000)). Alternatively, pluripotent stem cells may be cultured on a mouse embryonic fibroblast feeder cell layer according to the methods disclosed in Thompson et al (Science 6 Nov. 1998: Vol. 282. no. 5391, pp. 1145-1147). Alternatively, pluripotent stem cells may be cultured on any one of the feeder cell layers disclosed in Richards et al, (Stem Cells 21: 546-556, 2003).

In one embodiment, pluripotent stem cells may be cultured on a human feeder cell layer according to the methods disclosed in Wang et al (Stem Cells 23: 1221-1227, 2005). In an alternate embodiment, pluripotent stem cells may be cultured on the human feeder cell layer disclosed in Stojkovic et al (Stem Cells 2005 23: 306-314, 2005). Alternatively, pluripotent stem cells may be cultured on the human feeder cell layer disclosed in Miyamoto et al (Stem Cells 22: 433-440, 2004). Alternatively, pluripotent stem cells may be cultured on the human feeder cell layer disclosed in Amit et al (Biol. Reprod 68: 2150-2156, 2003). Alternatively, pluripotent stem cells may be cultured on the human feeder cell layer disclosed in Inzunza et al (Stem Cells 23: 544-549, 2005).

In one embodiment, pluripotent stem cells may be cultured in culture media derived according to the methods disclosed in US20020072117. Alternatively, pluripotent stem cells may be cultured in culture media derived according to the methods disclosed in U.S. Pat. No. 6,642,048. Alternatively, pluripotent stem cells may be cultured in culture media derived according to the methods disclosed in WO2005014799. Alternatively, pluripotent stem cells may be cultured in culture media derived according to the methods disclosed in Xu et al (Stem Cells 22: 972-980, 2004). Alternatively, pluripotent stem cells may be cultured in culture media derived according to the methods disclosed in US20070010011. Alternatively, pluripotent stem cells may be cultured in culture media derived according to the methods disclosed in US20050233446. Alternatively, pluripotent stem cells may be cultured in culture media derived according to the methods disclosed in U.S. Pat. No. 6,800,480. Alternatively, pluripotent stem cells may be cultured in culture media derived according to the methods disclosed in WO2005065354.

In one embodiment, pluripotent stem cells may be cultured in the culture media disclosed in WO2005065354. Alternatively, pluripotent stem cells may be cultured in the culture media disclosed in WO2005086845.

In one embodiment, pluripotent stem cells may be cultured according to the methods disclosed in Cheon et al (BioReprod DOI:10.1095/biolreprod.105.046870, Oct. 19, 2005). Alternatively, pluripotent stem cells may be cultured according to the methods disclosed in Levenstein et al (Stem Cells 24: 568-574, 2006). Alternatively, pluripotent stem cells may be cultured according to the methods disclosed in US20050148070. Alternatively, pluripotent stem cells may be cultured according to the methods disclosed in US20050244962. Alternatively, pluripotent stem cells may be cultured according to the methods disclosed in WO2005086845.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of Cells Expressing Markers Characteristic of the Definitive Endoderm Lineage from Pluripotent Stem Cells The present invention provides methods for the formation of populations of cells expressing markers characteristic of the definitive endoderm lineage from populations of pluripotent stem cells. In one embodiment, the present invention provides methods to further differentiate the cells expressing markers characteristic of the definitive endoderm lineage into cells expressing markers of the pancreatic endocrine lineage. In one embodiment, this is achieved utilizing a step-wise differentiation protocol, wherein populations of pluripotent stem cells are first differentiated into populations of cells expressing markers characteristic of the definitive endoderm lineage. Next, the populations of cells expressing markers characteristic of the definitive endoderm lineage are then differentiated into populations of cells expressing markers characteristic of the pancreatic endoderm lineage. Next, the populations of cells expressing markers characteristic of the pancreatic endoderm lineage are then differentiated into populations of cells expressing markers characteristic of the pancreatic endocrine lineage.

The present invention provides a population of cells wherein greater than 80% of the cells express markers characteristic of the definitive endoderm lineage. The population of cells may be further treated to form a population of cells expressing markers characteristic of the pancreatic endoderm lineage. The population of cells expressing markers characteristic of the pancreatic endoderm lineage may be further treated to form a population of cells expressing markers characteristic of the pancreatic endocrine lineage.

The efficiency of differentiation may be determined by exposing a treated cell population to an agent (such as an antibody) that specifically recognizes a protein marker expressed by cells expressing markers characteristic of the desired cell type.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, Nanog, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, Nanog, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF3 beta, MAFA, PAX4, and PAX6. In one aspect of the present invention, a cell expressing markers characteristic of the β cell lineage is a β cell.

Formation of Cells Expressing Markers Characteristic of the Definitive Endoderm Lineage from Pluripotent Stem Cells In one aspect of the present invention, populations of pluripotent stem cells may be differentiated into populations of cells expressing markers characteristic of the definitive endoderm lineage by culturing the pluripotent stem cells in a medium wherein the concentration of glucose does not exceed 10.5 mM. In one embodiment, differentiation of the population of pluripotent stem cells toward a population of cells expressing markers characteristic of the definitive endoderm lineage is achieved by treating the pluripotent stem cells with activin A and a Wnt ligand.

In an alternate embodiment, differentiation of the population of pluripotent stem cells toward a population of cells expressing markers characteristic of the definitive endoderm lineage is achieved by treating the pluripotent stem cells with GDF-8 and at least one other factor is selected from the group consisting of: an aniline-pyridinotriazine, a cyclic aniline-pyridinotriazine, N-{[1-(Phenylmethyl)azepan-4-yl]methyl}-2-pyridin-3-ylacetamide, 4-{[4-(4-{[2-(Pyridin-2-ylamino)ethyl]amino}-1,3,5-triazin-2-yl)pyridin-2-yl]oxy}butan-1-ol, 3-({3-[4-({2-[Methyl(pyridin-2-yl)amino]ethyl}amino)-1,3,5-triazin-2-yl]pyridin-2-yl}amino)propan-1-ol, N~4~-[2-(3-Fluorophenyl)ethyl]-N~2~-[3-(4-methylpiperazin-1-yl)propyl]pyrido[2,3-d]pyrimidine-2,4-diamine, 1-Methyl-N-[(4-pyridin-3-yl-2-{[3-(trifluoromethyl)phenyl]amino}-1,3-thiazol-5-yl)methyl]piperidine-4-carboxamide, 1,1-Dimethylethyl {2-[4-({5-[3-(3-hydroxypropyl)phenyl]-4H-1,2,4-triazol-3-yl}amino)phenyl]ethyl}carbamate, 1,1-Dimethylethyl {[3-({5-[5-(3-hydroxypropyl)-2-(methyloxy)phenyl]-1,3-oxazol-2-yl}amino)phenyl]methyl}carbamate, 1-({5-[6-({4-[(4-Methylpiperazin-1-yl)sulfonyl]phenyl}amino)pyrazin-2-yl]thiophen-2-yl}methyl)piperidin-4-ol, 1-({4-[6-({4-[(4-Methylpiperazin-1-yl)sulfonyl]phenyl}amino)pyrazin-2-yl]thiophen-2-yl}methyl)piperidine-4-carboxamide, and 2-{[4-(1-Methylethyl)phenyl]amino}-N-(2-thiophen-2-ylethyl)-7,8-dihydropyrido[4,3-d]pyrimidine-6(5H)-carboxamide. Examples of the factors suitable for use may be found in U.S. patent application Ser. No. 12/494,789. In one embodiment, the at least one other factor is 14-Prop-2-en-1-yl-3,5,7,14,17,23,27-heptaazatetracyclo[19.3.1.1~2,6~0.1~8,12~]heptacosa-1(25),2(27),3,5,8(26),9,11,21,23-nonaen-16-one.

The population of pluripotent stem cells may be cultured in the medium wherein the concentration of glucose does not exceed 10.5 mM for about one day to about seven days. Alternatively, the population of pluripotent stem cells may be cultured in the medium wherein the concentration of glucose does not exceed 10.5 mM for about one day to about six days. Alternatively, the population of pluripotent stem cells may cultured in the medium wherein the concentration of glucose does not exceed 10.5 mM for about one day to about five days. Alternatively, the population of pluripotent stem cells may cultured in the medium wherein the concentration of glucose does not exceed 10.5 mM for about one day to about four days. Alternatively, the population of pluripotent stem cells may be cultured in the medium wherein the concentration of glucose does not exceed 10.5 mM for about four days.

In one embodiment, the GDF-8 is used at a concentration from about 5 ng/ml to about 500 ng/ml. In an alternate embodiment, the GDF-8 is used at a concentration from about 5 ng/ml to about 50 ng/ml. In an alternate embodiment, the GDF-8 is used at a concentration from about 5 ng/ml to about 25 ng/ml. In an alternate embodiment, the GDF-8 is used at a concentration of about 25 ng/ml.

Activin-A may be used at a concentration from about 1 pg/ml to about 100 µg/ml. In an alternate embodiment, the concentration may be about 1 pg/ml to about 1 µg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be used at a concentration of about 1 ng/ml to about 1000 ng/ml. In an alternate embodiment, the Wnt ligand may be used at a concentration of about 10 ng/ml to about 100 ng/ml. In one embodiment, the concentration of the Wnt ligand is about 20 ng/ml.

Formation of Cells Expressing Markers Characteristic of the Pancreatic Endoderm Lineage In one embodiment, populations of cells expressing markers characteristic of the definitive endoderm lineage formed by the methods of the present invention are further differentiated into populations of cells expressing markers characteristic of the pancreatic endoderm lineage by any method in the art.

For example, populations of cells expressing markers characteristic of the definitive endoderm lineage obtained according to the methods of the present invention may be further differentiated into populations of cells expressing markers characteristic of the pancreatic endoderm lineage by treating the population of cells expressing markers characteristic of the definitive endoderm lineage according to the methods disclosed in D'Amour et al, Nature Biotechnology 24, 1392-1401 (2006).

For example, populations of cells expressing markers characteristic of the definitive endoderm lineage obtained according to the methods of the present invention may be further differentiated into populations of cells expressing markers characteristic of the pancreatic endoderm lineage by treating the population of cells expressing markers characteristic of the definitive endoderm lineage according to the methods disclosed in U.S. patent application Ser. No. 11/736,908.

Formation of Cells Expressing Markers Characteristic of the Pancreatic Endocrine Lineage In one embodiment, populations of cells expressing markers characteristic of the pancreatic endoderm lineage are further differentiated into populations of cells expressing markers characteristic of the pancreatic endocrine lineage by any method in the art.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in D' Amour et al, Nature Biotechnology, 2006.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed d in D' Amour et al, Nature Biotechnology, 2006.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 11/736,908.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 11/779,311.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 60/953,178.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 60/990,529.

The present invention is further illustrated, but not limited by, the following examples.

EXAMPLES

Example 1

The Role of Media and Seeding Protocol in the Differentiation of Human Pluripotent Stem Cells to Cells Expressing Markers Characteristic of the Definitive Endoderm Lineage Cells of the human embryonic stem cell line H1 at passage 41 (p41) were lifted by TrypLE (Catalog#12604-013, Invitrogen, CA) and seeded as single cells at a density of 100,000 cells/cm$^2$ on MATRIGEL® coated dishes (1:30 dilution) in MEF-CM (mouse embryonic fibroblast conditioned media) supplemented with 20 ng/ml FGF2 (Catalog#100-18B, PeproTech, NJ) and 10 µM of Y-27632 (a Rho Kinase Inhibitor, Catalog#Y0503, Sigma, MO).

In parallel, cells of the human embryonic stem cell line H1 at passage 41 were seeded as cell colonies MATRIGEL® coated dishes (1:30 dilution) at a 1 to 3 passage ratio by lifting cells with Dispase (Catalog#17105-041, Invitrogen, CA) and plating the cells in MEF-CM with 20 ng/ml FGF2. For both single cell and colony format cultures the media was changed 24 and 48 hours post seeding with fresh MEF-CM with 20 ng/ml FGF2.

At 72 hrs post seeding, the cultures were differentiated into cells expressing markers characteristic of the definitive endoderm lineage as follows:

a. MCDB-131 (Catalog#10372-019, Invitrogen, CA) containing an additional 0.0025 g/ml sodium bicarbonate (Catalog#S3187, Sigma, MO), was supplemented with 2% fatty acid-free BSA (Catalog#68700, Proliant, IA), 1× GlutaMax™ (Catalog #35050-079, Invitrogen, Ca) and 100 ng/ml activin A (R&D Systems, Minn.) plus 20 ng/ml WNT-3a (Catalog#1324-WN-002, R&D Systems, MN.) for one day, then MCDB-131 with an additional 0.0025 g/ml sodium bicarbonate, 2% BSA, Glutamax, and 100 ng/ml activin A for three days (Condition 1); or, b. RPMI-1640 (Catalog #22400-105, Invitrogen, CA), was supplemented with 2% fatty acid-free BSA (Catalog#68700, Proliant, IA), and 100 ng/ml activin A (R&D Systems, MN) plus 20 ng/ml WNT-3a (Catalog#1324-WN-002, R&D Systems, MN), for one day, then RPMI-1640 medium supplemented with 2% BSA, and 100 ng/ml activin A each day for an additional three days (Condition 2).

At day 4, samples were collected for FACS analysis. In FIG. 1, the flow cytometry results for CXCR4 and CD9 expression are shown in scatter plot format with CXCR4 expression plotted on the Y axis versus CD9 expression plotted on the X axis. The percentage of cells expressing CXCR4, CD9, and CD99 (an additional marker of differentiation) are summarized in Table 1. Differentiation, as measured by the increased expression of the cellular surface markers CXCR4 and CD99, was improved by the use of MCDB-131 media, and expression of CXCR4 and CD99 was further increased by changing from colony style culture to a single cell culture. Furthermore, these data correlated with decreased expression of CD9, a cellular marker for undifferentiated cells, as measured by flow cytometry.

Interestingly, with the use of MCDB-131 in either cluster or colony style format, there are fewer co-negative (CXCR4$^-$/CD9$^-$) cells in FIG. 1, indicating less non-specific differentiation, or fewer cells that do not express markers characteristic of the definitive endoderm lineage in cultures treated MCDB-131 medium. As a whole, these data indicate that H1 human embryonic stem cells differentiate more efficiently in the presence of MCDB-131 medium than RPMI-1640 medium, and that differentiation in MCDB-131 can be further improved by seeding and culturing the cells as single cells versus colony style seeding and culture.

TABLE 1

|  | CXCR4 | CD9 | CD99 |
|---|---|---|---|
| MCDB (cluster) | 88.6 | 10.1 | 21.7 |
| RPMI (cluster) | 81.8 | 8.8 | 30.5 |
| MCDB (single cell) | 92.3 | 6.7 | 62.2 |
| RPMI (single cell) | 72.4 | 12.7 | 43.1 |

Example 2

The Role of Glucose in the Differentiation of Human Pluripotent Stem Cells to Cells Expressing Markers Characteristic of the Definitive Endoderm Lineage Glucose is a soluble hexose sugar added to almost all cell culture media including Ames'Medium; Basal Medium Eagle (BME); BGJb Medium Fitton-Jackson Modification; Click's Medium; CMRL-1066 Medium; Dulbecco's Modified Eagle's Medium (DMEM); DMEM/Ham's Nutrient Mixture F-12 (50:50); F-12 Coon's Modification; Fischer's Medium; H-Y Medium (Hybri-Max®); Iscove's Modified Dulbecco's Medium (IMDM); McCoy's 5A Modified Medium; MCDB Media; Medium 199; Minimum Essential Medium Eagle (EMEM); NCTC Medium; Nutrient Mixture, Ham's F-10; Nutrient Mixture, Ham's F-12; Nutrient Mixture Ham's F-12 Kaighn's Modification (F12K); RPMI-1640; Serum-Free/Protein Free Hybridoma Medium; Waymouth Medium MB; Williams Medium E and various proprietary media. See http://www.sigmaaldrich.com/life-science/cell-culture/learning-center/media-expert/glucose.html.

The amount of glucose in cell culture formulations varies. While the MCDB media series contain glucose in the range from 3.9 to 10 mM, most media contain from 1 g/L (5.5 mM) to as high as 10 g/L (55 mM) glucose, with RPMI-1640 set at 11 mM glucose. Concentrations of glucose above 10 mM are analogous to a diabetic condition within the cell culture system. This is important because the same processes that can affect cells and molecules in vivo can occur in vitro. The consequence of growing cells under conditions that are essentially diabetic is that cells and cell products are modified by the processes of glycation and glyoxidation and can be damaged by glucose mediated oxidative and carbonyl stress. See http://www.sigmaaldrich.com/life-science/cell-culture/learning-center/media-expert/glucose.html.

One medium that is currently used for generating definitive endoderm is Iscove's Modified Dulbecco's Medium (IMDM) which contains 25 mM glucose (Kubo et al; Apr. 1, 2004, Development 131, 1651-1662), RPMI with 11 mM glucose (D'Amour et al Nat Biotechnol. 2005 December; 23(12):1534-41), or DMEM-F12 with 17.5 mM glucose. Each of these media is above the 10 mM glucose concentration analogous to a diabetic condition. Consequently, to reduce stress on the cells that might be induced by high glucose in the culture medium, we attempted to find a glucose concentration lower than 10 mM for differentiation of human embryonic stem cells to cells expressing markers characteristic of the definitive endoderm lineage. One such medium with a glucose concentration below 10 mM is MCDB-131 which contains a base glucose concentration of 5.5 mM.

Cells of the human embryonic stem cell line H1 at passage 41 (p41) were lifted by TrypLE (Catalog# 12604-013, Invitrogen, CA) and seeded as single cells at a density of 100,000 cells/cm$^2$ on MATRIGEL® coated dishes (1:30 dilution) in MEF-CM (mouse embryonic fibroblast conditioned media) supplemented with 20 ng/ml of FGF2 (Catalog# 100-18B, PeproTec$^h$, NJ) and 10 µM of Y-27632 (a Rho Kinase Inhibitor, Catalog# Y0503, Sigma, MO). The media was changed 24 and 48 hours post seeding with fresh MEF-CM with 20 ng/ml of FGF2. The cultures were differentiated into cells expressing markers characteristic of the definitive endoderm lineage 72 hrs post as follows:

a. MCDB-131 (Catalog# 10372-019, Invitrogen, CA) medium supplemented with 2% fatty acid-free BSA (Catalog# 68700, Proliant, IA), 0.0025 g/ml sodium bicarbonate (Catalog# S3187, Sigma, MO), 1X GlutaMax™ (Catalog # 35050-079, Invitrogen, Ca) 100 ng/ml activin A (R&D Systems, MN), 20 ng/ml WNT-3a (Catalog# 1324-WN -$^0$02, R&D Systems, MN), and either 0, 5, 10, 15, 20, or 25mM of glucose (Catalog# G8769,Sigma, MO) for one day, then b. MCDB-131 medium supplemented with 2% BSA, sodium bicarbonate, Glutamax, 100 ng/ml activin A, and either 0, 5, 10, 15, 20, or 25mM of glucose for an additional three days.

Figure 2A:
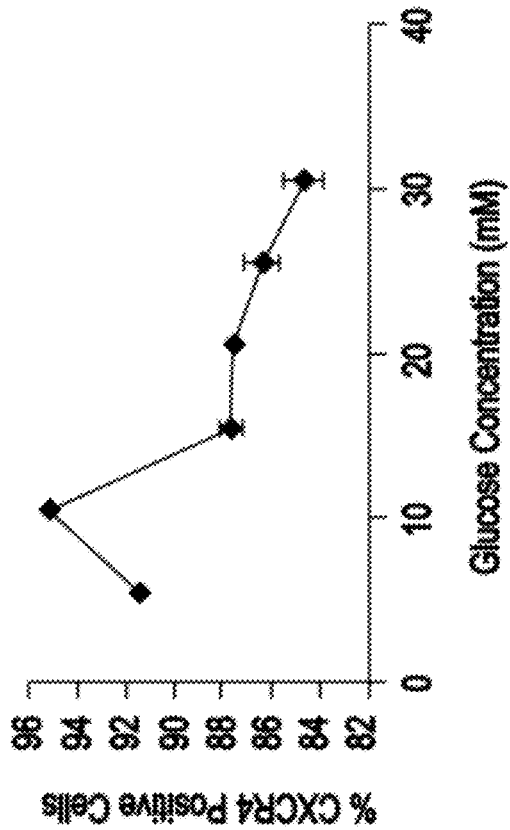

At day 4, samples were collected for FACS and gene expression analysis using real-time PCR, and counted by ViaCount® (Guava®, Millipore, Billerica, Mass.). Consistent with results from Example 1, differentiation of pluripotent stem cells to cells expressing markers characteristic of the definitive endoderm lineage resulted in the robust expression of markers associated with the definitive endoderm lineage (FIG. 2A). When the glucose concentration in the media was supplemented with 0, 5, 10, 15, 20, or 25 mM glucose (final concentration: 5.5, 10.5, 15.5, 20.5, 25.5, or 30.5 mM glucose respectively), a modest increase in cell number was observed in samples treated with additional 10 mM glucose (15.5 mM final glucose concentration) as shown in FIG. 2B. A modest increase in CXCR4 expression for cells supplemented with additional 5 mM glucose (10.5 mM final glucose concentration) was also observed, as shown in FIG. 2A. However, these increases in cell number and CXCR4 were offset by a reduction in total cell viability (FIG. 2B).

Figure 4:
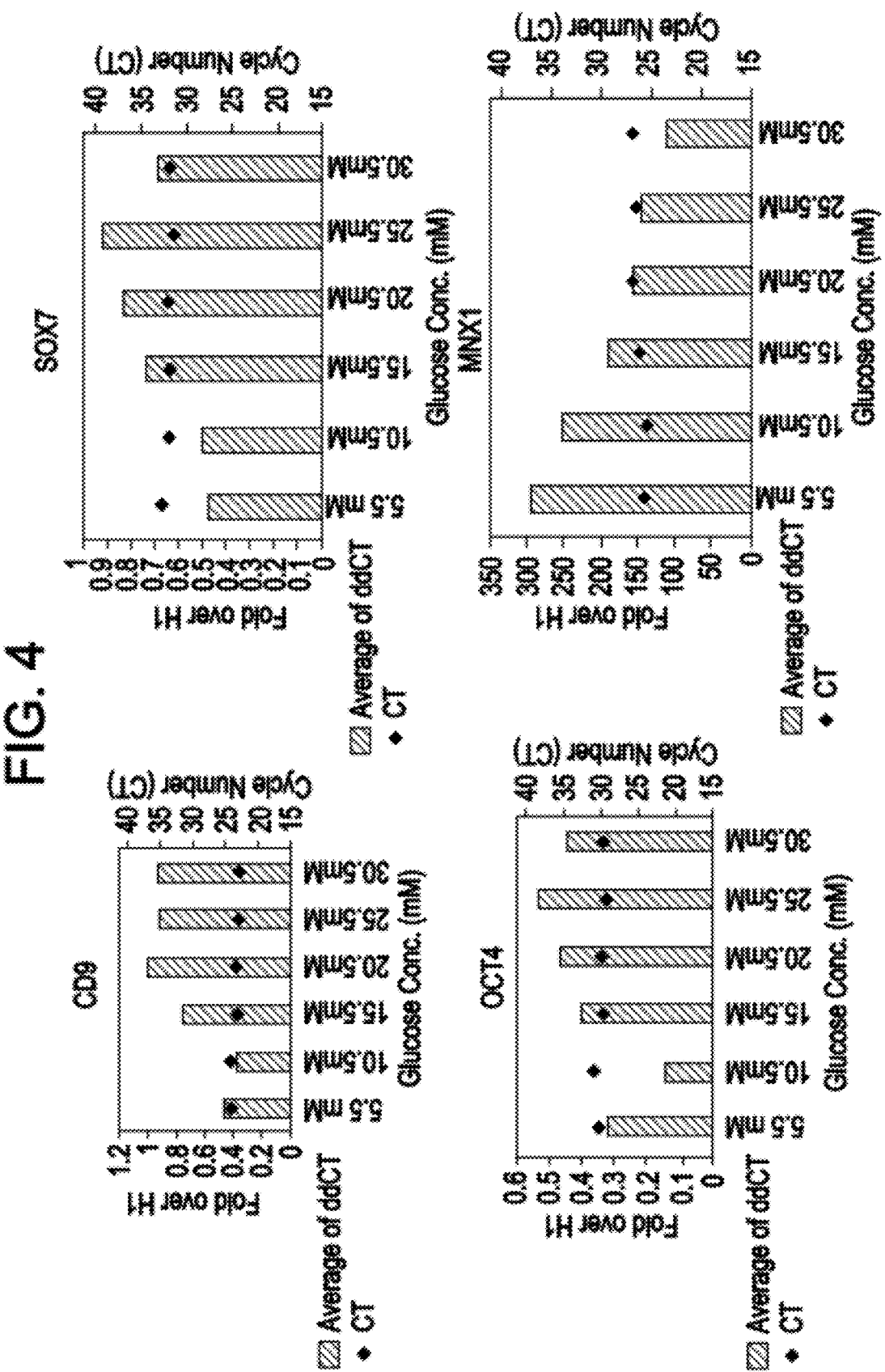
FIG. 4 shows the real-time PCR analysis of the expression of the genes indicated in cells of the human embryonic stem cell line H1, differentiated according to the first method disclosed in Example 2.

At the basal level of glucose (5.5 mM), almost every cell in the culture was SOX17 positive, and the cells were dispersed in the culture dish in a uniform pattern (FIG. 3 A&B). As the glucose concentration increased, the cells maintained a high expression of SOX17, however the cells were observed to cluster. These clustered cells were subsequently less evenly dispersed on the culture surface than populations of cells cultured in the basal level of glucose. This effect correlated with a slight increase in expression of CD9 and OCT4– cellular markers for undifferentiated cells, and SOX7– a cellular marker for extraembryonic ectoderm, and a decrease in the gene expression of pancreatic pancreas homeobox 1 (MNX1) also known as Homeobox HB9 (HLXB9) in the clustered cells (FIG. 4).

Similar glucose related effects on differentiation were also observed in cultures differentiated with DMEM containing either 5.5 mM (low) or 25 mM (high) glucose concentration (Cat#s 10567-014 and 21063-029, Invitrogen, CA). As described above, for controls, cells were seeded as single cells, cultured 3 days in MEF conditioned media and differentiated in MCDB-131 with 5.5 mM or 25 mM glucose supplemented media, or in DMEM high or low glucose media supplemented with 2% fatty acid free BSA, 100 ng/ml activin A, and 20 ng/ml WNT-3a on the first day, and 2% fatty acid free BSA and 100 ng/ml activin A for the next three days with daily media change.

Figure 5:
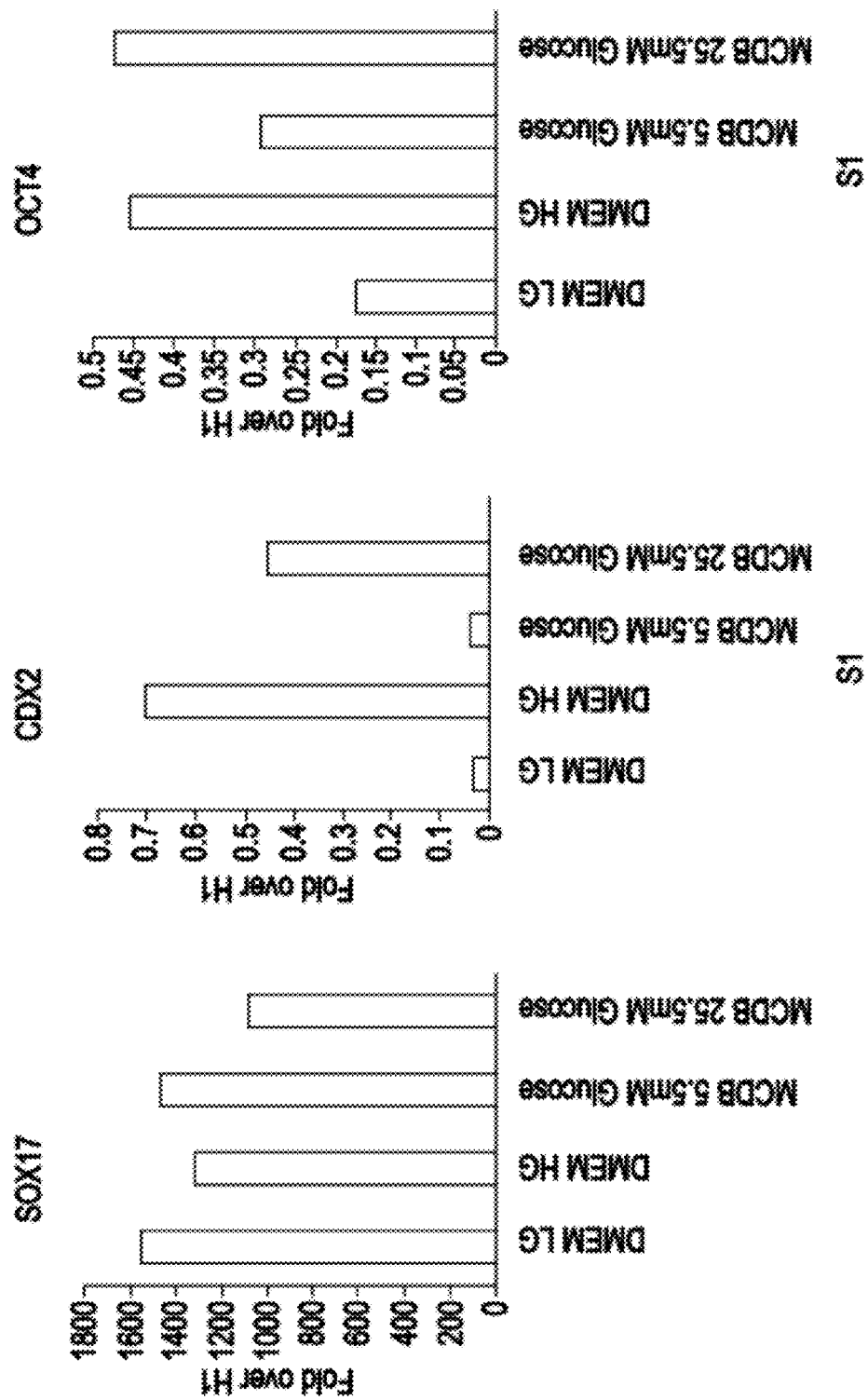
FIG. 5 shows the real-time PCR analysis of the expression of the genes indicated in cells of the human embryonic stem cell line H1, differentiated according to the second method disclosed in Example 2.
Figure 6:
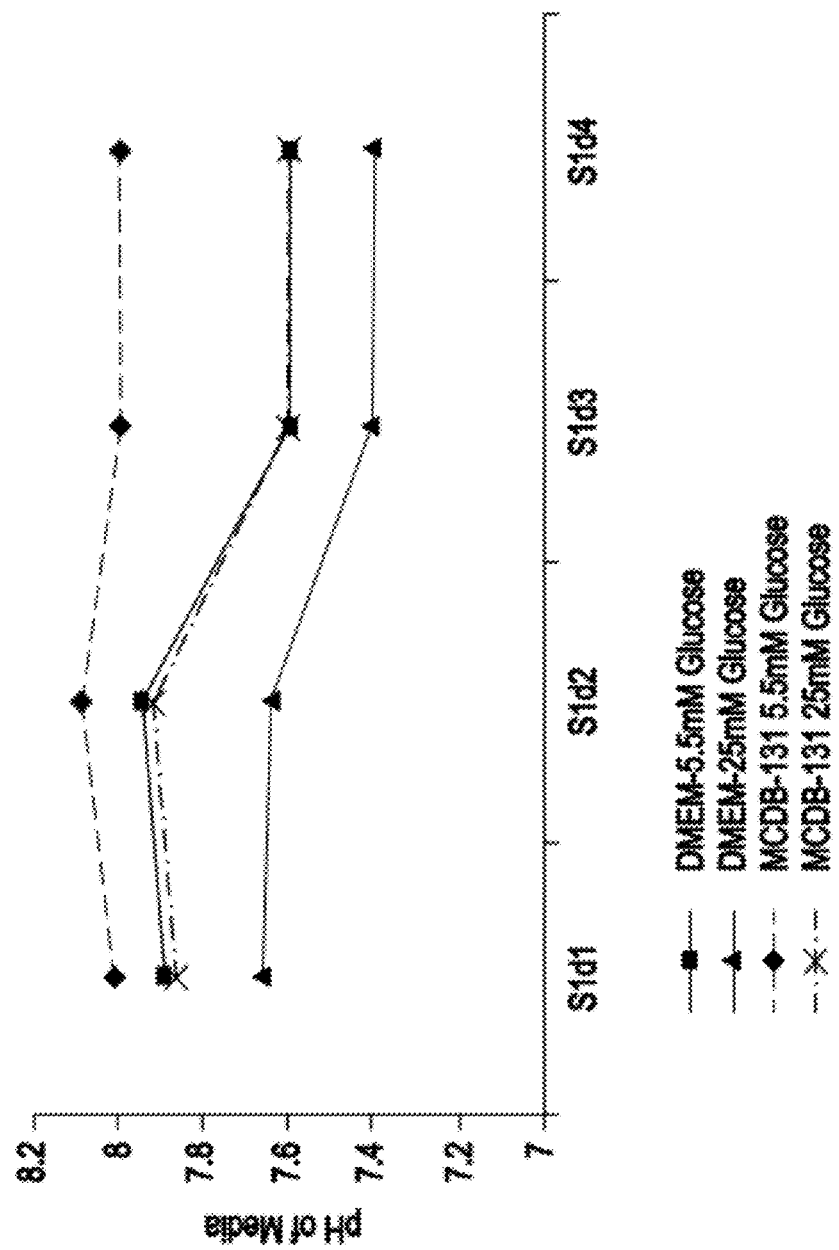
FIG. 6 shows the pH level of the various media following a 24 hour exposure to cells on days 1 through 4 of the methods disclosed in Example 2.

Similar to results with MCDB-131 media, where elevated glucose inhibits definitive endoderm formation as compared to low glucose media treated cells, we observed that a high glucose concentration in DMEM reduced hES cell differentiation. By flow cytometry, following differentiation to definitive endoderm, 88.6% of cells were positive for CXCR4 in media containing 5.5 mM glucose versus 80% CXCR4 positive cells in media containing 25 mM glucose. Additionally, markers of differentiation to definitive endoderm as measured by qRT-PCR (SOX17) were decreased while markers of undifferentiated cells (OCT4) or alternative differentiation fates (CDX2) were increased (FIG. 5) in cells fed media containing high glucose versus those fed low glucose media. This effect was due at least in part to the pH of the media as we noted that over the four day differentiation, media pH dropped after 48 hours of differentiation day. Furthermore, the higher the starting and ending pH of culture media (8.1>pH>7.6) (FIG. 6) during definitive endoderm formation, the more complete the conversion to definitive endoderm.

In summary, our results indicate that basal levels of glucose (5.5 mM) in differentiation media are sufficient to generate a population of cells wherein greater than 80% of cells express markers characteristic of the definitive endoderm lineage. Increasing glucose concentrations in the differentiation medium to 10.5 mM is sufficient to generate a similar population, however increasing glucose concentrations above 10.5 mM can result in increasing expression of markers of pluripotency/reduced differentiation such as CD9 or OCT4, or increased expression of markers associated with alternative fate differentiation/extraembryonic ectoderm such as SOX7 or CDX2.

Example 3

The Role of pH Control in the Differentiation of Human Pluripotent Stem Cells to Cells Expressing Markers Characteristic of the Definitive Endoderm Lineage Cells of the human embryonic stem (hES) cell line H1 at passage 46 (p46) were seeded as cell colonies to MATRIGEL (1:30 dilution) coated dishes at a 1 to 3 passage ratio by lifting cells with Dispase (Catalog#17105-041, Invitrogen, CA) and plating the cells in MEF-CM with 20 ng/ml of FGF2. The media was changed daily with fresh MEF-CM with 20 ng/ml of FGF2, until initiation of differentiation into definitive endoderm (DE) as follows:

a. MCDB-131 (Catalog#10372-019, Invitrogen, CA) medium supplemented with 2% fatty acid-free BSA (Catalog#68700, Proliant, IA), 1× GlutaMax™ (Catalog #35050-079, Invitrogen, Ca) and 100 ng/ml activin A (R&D Systems, MN) plus 20 ng/ml WNT-3a (Catalog#1324-WN-002, R&D Systems, MN) for one day, followed by treatment with MCDB-131 supplemented with 2% BSA, Glutamax, and 100 ng/ml activin A each day for an additional three days; or b. MCDB131 containing an additional 0.0025 g/ml sodium bicarbonate (Catalog#S3187, Sigma, MO) medium supplemented with 2% fatty acid-free BSA (Catalog#68700, Proliant, IA), 1× GlutaMax™ (Catalog #35050-079, Invitrogen, Ca) and 100 ng/ml activin A (R&D Systems, MN.) plus 20 ng/ml WNT-3a (Catalog#1324-WN-002, R&D Systems, MN) for one day, followed by treatment with MCDB-131 with an additional 0.0025 g/ml sodium bicarbonate supplemented with 2% BSA, Glutamax, and 100 ng/ml activin A each day for an additional three days.

At day 4, samples were collected for FACS and gene expression analysis using real-time PCR, and counted by ViaCount® (Guava®, Millipore, Billerica, Mass.). As shown in Example 2, we noted that a relatively more acidic pH of differentiation media (<7.6 pH) can reduce CXCR4 expression due to less directed differentiation and increased alternative differentiation.

In order to test if this effect was due to pH, we differentiated cells in basal MCDB-131 that contains the published concentration of 1 gram/liter of sodium bicarbonate and we differentiated cells in media supplemented to the bicarbonate concentration of DMEM, which is 3.7 grams/liter. We observed that differentiation, as measured by the increased expression of the cellular surface markers CXCR4 and decreased expression of CD9, was improved by the use of a buffering agent. MCDB-131 media with 3.7 g/l of Sodium Bicarbonate for a buffer had significantly higher CXCR4 expression and lower CD9 expression levels versus cells differentiated in MCDB-131 that contained only the base level of Bicarbonate (1 g/l) (FIGS. 7A and B). This is due in part to the fact that MCDB-131 media has a pH level of 7.5, and addition of 2.7 g/l of Sodium Bicarbonate raises the pH to 7.6.

Furthermore, at the end of differentiation, the media (containing the pH color sensor phenol red) from cultures grown in undifferentiated media were significantly more yellow and acidic than cultures with supplemental sodium bicarbonate buffered media which remained red in color.

These results indicate that increasing media pH to 7.6 or higher promotes more efficient definitive endoderm differentiation from pluripotent stem cells, and raising and stabilizing media pH could be achieved by alternatives to bicarbonate buffering including, but not limited to, increasing incubator $CO_2$ levels and other soluble buffer systems like HEPES, or phosphate.

Example 4

The Role of RPMI-1640 or MCDB-131 Media and the TGF-Beta Superfamily Members Activin A and GDF-8 in the Differentiation of Human Pluripotent Stem Cells to Cells Expressing Markers Characteristic of the Definitive Endoderm Lineage Cells of the human embryonic stem cell line H1 at passage 47 (p47) were lifted by TrypLE (Catalog#12604-013, Invitrogen, CA) and seeded as single cells at a density of 100,000 cells/cm$^2$ on MATRIGEL® coated dishes (1:30 dilution) in MEF-CM (mouse embryonic fibroblast conditioned media) supplemented with 20 ng/ml FGF2 (Catalog#100-18B, PeproTech, NJ) and 3 µM of H-1152, glycyl (a Rho Kinase Inhibitor, Catalog#555554, EMD chemicals, Gibbstown, N.J.).

At 72 hrs post seeding, the cultures were differentiated into cells expressing markers characteristic of the definitive endoderm lineage as follows:
a. MCDB-131 (Catalog#10372-019, Invitrogen, CA) containing an additional 0.0025 g/ml sodium bicarbonate (Catalog#S3187, Sigma, MO), was supplemented with 2% fatty acid-free BSA (Catalog#68700, Proliant, IA), 1× GlutaMax™ (Catalog #35050-079, Invitrogen, Ca) and 100 ng/ml activin A (R&D Systems, MN) plus 20 ng/ml WNT-3a (Catalog#1324-WN-002, R&D Systems, MN) for one day, then MCDB-131 with an additional 0.0025 g/ml sodium bicarbonate, 2% BSA, Glutamax, and 100 ng/ml activin A for three days, or,
b. MCDB-131 (Catalog#10372-019, Invitrogen, CA) containing an additional 0.0025 g/ml sodium bicarbonate (Catalog#S3187, Sigma, MO), was supplemented with 2% fatty acid-free BSA (Catalog#68700, Proliant, IA), 1× GlutaMax™ (Catalog #35050-079, Invitrogen, Ca) and 100 ng/ml GDF-8 (R&D Systems, MN) plus 2.5 µM of the GSK3B inhibitor 14-Prop-2-en-1-yl-3,5,7,14,17,23,27-heptaazatetracyclo[19.3.1.1~2,6~0.1~8,12~]heptacosa-1(25),2(27),3,5,8(26),9,11,21,23-nonaen-16-one for one day, then MCDB-131 with an additional 0.0025 g/ml sodium bicarbonate, 2% BSA, Glutamax, and 100 ng/ml GDF-8 for three days, or,
c. MCDB-131 (Catalog#10372-019, Invitrogen, CA) containing an additional 0.0025 g/ml sodium bicarbonate (Catalog#S3187, Sigma, MO), was supplemented with 2% fatty acid-free BSA (Catalog#68700, Proliant, IA), 1× GlutaMax™ (Catalog #35050-079, Invitrogen, Ca) and 100 ng/ml GDF-8 (R&D Systems, MN) for four days, or,
d. RPMI-1640 (Catalog #22400-105, Invitrogen, CA), was supplemented with 2% fatty acid-free BSA (Catalog#68700, Proliant, IA), and 100 ng/ml activin A (R&D Systems, MN) plus 20 ng/ml WNT-3a (Catalog#1324-WN-002, R&D Systems, MN), for one day, then RPMI-1640 medium supplemented with 2% BSA, and 100 ng/ml activin A each day for an additional three days.
e. RPMI-1640 (Catalog #22400-105, Invitrogen, CA), was supplemented with 2% fatty acid-free BSA (Catalog#68700, Proliant, IA), and 100 ng/ml GDF-8 (R&D Systems, MN) plus 2.5 µM of the GSK3B inhibitor 14-Prop-2-en-1-yl-3,5,7,14,17,23,27-heptaazatetracyclo[19.3.1.1~2,6~0.1~8,12~]heptacosa-1(25),2(27),3,5,8(26),9,11,21,23-nonaen-16-one for one day, then RPMI-1640 medium supplemented with 2% BSA, and 100 ng/ml GDF-8 each day for an additional three days.

At day 4, samples were collected for FACS analysis and qRT-PCR. In Table 2, the percentage of cells expressing CXCR4, CD9, and CD99 (an additional marker of differentiation) are summarized in Table 2. Differentiation, as measured by the increased expression of the cellular surface marker CXCR4 was improved by the use of MCDB-131 media compared to RPMI-1640, and expression of CXCR4 was further increased by using GDF-8 in combination with GSK3B inhibitor ("MCX"), compared to cells treated with activin A and Wnt3a. Similar results, showing improved differentiation with the use of MCDB-131 media compared to RPMI-1640, and by using GDF-8 in combination with a GSK3B inhibitor compared to cells treated with activin A and Wnt3a were observed by qRT-PCR for the gene MNX-1 (FIG. 8). Furthermore, these data correlated with decreased expression of CD9, a cellular marker for undifferentiated cells, as measured by flow cytometry (Table 2) or OCT4 and CD9, as measured by qRT-PCR (FIG. 8). These data indicate that H1 human embryonic stem cells differentiate more efficiently in the presence of MCDB-131 medium than RPMI-1640 medium, and that differentiation in MCBD-131 can be further improved by differentiating the cells in the presence of GDF-8 and a GSK3B inhibitor versus differentiation with activin A and Wnt3a.

TABLE 2

| Media Treatment | CD184 | CD9 | CD99 |
| --- | --- | --- | --- |
| RPMI + AA + Wnt | 77.8 | 20.9 | 77.8 |
| RPMI + GDF8 + GSK3B inhibitor | 81.6 | 13.8 | 83.4 |
| MCDB131 + AA + Wnt | 81.2 | 21.1 | 60.0 |
| MCDB131 + GDF8 + GSK3B inhibitor | 87.1 | 14.3 | 50.9 |
| MCDB131 + GDF8 | 43.2 | 31.2 | 23.7 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:
1. An in vitro culture comprising an isolated population of in vitro differentiated cells and a serum-free cell culture medium supplemented with L-alanyl-L-glutamine in which the concentration of glucose does not exceed 10.5 mM,
   wherein greater than 80% of the cells in the population are definitive endoderm cells and express CXCR4 and CD99, and
   wherein said population of cells is obtained by a step-wise differentiation process comprising:
   (i) seeding clusters of pluripotent stem cells in a serum-free medium supplemented with L-alanyl-L-glutamine, and glucose at a concentration that does not exceed 10.5 mM;
   (ii) culturing the pluripotent stem cells for about one day in a serum-free medium supplemented with L-alanyl-L-glutamine, about 100 ng/ml activin A, about 20 ng/ml of Wnt-3a, and glucose at a concentration that does not exceed 10.5 mM; followed by

(iii) culturing the cells for about three days in a serum-free medium supplemented with L-alanyl-L-glutamine, about 100 ng/ml activin A, and glucose at a concentration that does not exceed 10.5 mM, whereby the culture does not require further purification or selection of the definitive endoderm cells.

2. The isolated population of cells of claim 1, wherein the concentration of glucose does not exceed 5.5 mM.

3. An in vitro culture comprising an isolated population of in vitro differentiated cells and a serum-free cell culture medium supplemented with L-alanyl-L-glutamine and glucose at a concentration that does not exceed 10.5 mM,
  wherein greater than 80% of the cells in the population are definitive endoderm cells and express CXCR4 and, CD99, and
  wherein said population of cells is obtained by a step-wise differentiation process comprising the steps of:
  (i) seeding pluripotent stem cells in a serum-free medium supplemented with L-alanyl-L-glutamine and glucose at a concentration that does not exceed 10.5 mM,
  (ii) culturing the pluripotent stem cells for about one day in a serum-free medium supplemented with L-alanyl-L-glutamine, about 100 ng/ml activin A, about 20 ng/ml Wnt-3a and glucose at a concentration that does not exceed 10.5 mM; followed by
  (iii) culturing the cells for about three days in a serum-free medium supplemented with L-alanyl-L-glutamine, about 100 ng/ml activin A, and glucose at concentration that does not exceed 10.5 mM, whereby the culture does not require further purification or selection of the definitive endoderm cells.

4. The in vitro culture of claim 3, wherein the concentration of glucose does not exceed 5.5 mM.

5. The in vitro culture of claim 3, wherein the concentration of glucose in said step-wise differentiation process does not exceed 5.5 mM.

6. A method for generating a population of cells wherein 80% of the cells in the population are definitive endoderm cells and express CXCR4 and CD99, wherein said population of cells is obtained by a step-wise differentiation process comprising the steps of:
  (i) seeding pluripotent stem cells in a serum-free medium supplemented with L-alanyl-L-glutamine and glucose at a concentration that does not exceed 10.5 mM,
  (ii) culturing the pluripotent stem cells for about one day in a serum-free medium supplemented with L-alanyl-L-glutamine, about 100 ng/ml activin A, about 20 ng/ml Wnt-3a and glucose at a concentration that does not exceed 10.5 mM; followed by
  (iii) culturing the cells for about three days in a serum-free medium supplemented with L-alanyl-L-glutamine, about 100 ng/ml activin A, and glucose at concentration that does not exceed 10.5 mM, whereby the culture does not require further purification or selection of the definitive endoderm cells.

* * * * *